United States Patent
Watanabe

(10) Patent No.: US 6,747,276 B2
(45) Date of Patent: Jun. 8, 2004

(54) INTERFERENCE FILTER TRANSMISSION WAVELENGTH SCANNING PHOTOMETER

(76) Inventor: Atsuo Watanabe, 602, Asahigaoka Heights, 2-24, Asahigaoka 3-chome, Hino-shi, Tokyo (JP), 191-0065

( * ) Notice: Subject to any disclaimer, the term of this patent is extended or adjusted under 35 U.S.C. 154(b) by 328 days.

(21) Appl. No.: 09/959,454

(22) PCT Filed: Feb. 27, 2001

(86) PCT No.: PCT/JP01/01455
§ 371 (c)(1), (2), (4) Date: Oct. 26, 2001

(87) PCT Pub. No.: WO01/63249
PCT Pub. Date: Aug. 30, 2001

(65) Prior Publication Data
US 2002/0190211 A1 Dec. 19, 2002

(30) Foreign Application Priority Data
Feb. 28, 2000 (JP) ......................... 2000-051329

(51) Int. Cl.[7] ............................................. G01N 21/17
(52) U.S. Cl. ........................ 250/343; 250/340; 250/372
(58) Field of Search ............................... 250/343, 347, 250/372, 373, 340, 339.01, 350, 351

(56) References Cited
U.S. PATENT DOCUMENTS
4,752,129 A * 6/1988 Izumi et al. ................ 356/328
5,268,745 A * 12/1993 Goody ........................ 356/418

FOREIGN PATENT DOCUMENTS
JP 2-240546 9/1990
JP 5-267770 10/1993

* cited by examiner

*Primary Examiner*—Constantine Hannaher
*Assistant Examiner*—Timothy Moran
(74) *Attorney, Agent, or Firm*—Wenderoth, Lind & Ponack, L.L.P.

(57) ABSTRACT

An interference filter transmission wavelength scanning photometer operable to determine the concentration of an interesting component in a sample without interference from coexisting components by measuring the light absorption of the interesting component. An angle of inclination of an interference filter varies periodically and is centered at the maximum absorption wavelength of the interesting component. The wavelength of a transmitted light is modulated due to the periodical variation of the angle of inclination. Variation in the intensity of the light transmitted through a sample is extracted by an infrared sensor as an electric signal. The time between rise and fall zero cross points of an AC component of the electric signal is determined by a microprocessor. A ratio is calculated from a full period and a half period of the AC component. The concentration of the interesting component is determined from a variation in the calculation of the ratio.

14 Claims, 8 Drawing Sheets

Glucose concentration in the blood measured by
The commercial glucose meter

INTERFERENCE FILTER TRANSMISSION WAVELENGTH SCANNING PHOTOMETER

BACKGROUND OF THE INVENTION

1. Field of the Invention

The present invention relates to a convenient and inexpensive analytical apparatus for determining the concentration of an interesting component in a sample without interference from coexistent components by measuring the light absorption of the interesting component.

More particularly, the present invention relates to the convenient and inexpensive analytical apparatus which is realized by the procedures of:

preparing an interference filter that has means for scanning a transmission wavelength periodically;

detecting a change in the intensity of light whose wavelengths are scanned by the interference filter and which transmit through the sample; and determining a concentration of the interesting component by periodically examining the detected electric signal.

2. Description of the Related Art

It is well-known to detect an interesting component in a sample or to determine its concentration by measuring the light absorption of the interesting component. The simplest known method is to measure intensity changes of a monochromatic light transmitting through the sample in which the interesting component absorbing the monochromatic light is contained. For instance, an ultraviolet absorption photometer for monitoring water quality is well-known. This photometer utilizes a phenomenon in which an organic waste in water absorbs light of 253.7 nm from a mercury lamp, and the photometer consists of a light source, a sample cell, a detector and an amplifier. By this method, which is referred to as a single beam method, there often exists a measuring error because an interfering value due to a change in the intensity of the light source is not able to be distinguished from a measured value due to the light absorption of the organic waste.

There exists a double beam method which removes this defect of the single beam method. In the double beam method, a beam from a light source splits into two beams in which one of the beams is for a sensing beam and the other beam is for a reference beam, and the measured value is obtained as the difference or ratio between the intensities of these two beams. The intensity change of the sensing beam is standardized by the intensity of the reference beam. By adopting the double beam method, a change in the intensity of the light source does not affect the measured results.

Double wavelength spectrometry is another method which does not affect the measured results due to a change in the intensity of the light source. In this method, two different monochromatic beams are alternately transmitted through or reflected on a sample, and the absorption intensity of an interesting component in the sample is obtained by measuring the difference or ratio between the intensities of the two monochromatic beams. A wavelength of the one monochromatic beam for reference is selected separately from an absorption wavelength of the interesting component, and a wavelength of the other monochromatic beam for sensing is equal to the absorption wavelength of the interesting component. The intensity change of the monochromatic beam for sensing is standardized by the intensity of the monochromatic beam for reference. Therefore, this method does not have a measuring error due to a change in the intensity of the light source.

As the present invention is aimed at developing an apparatus which does not have a measuring error due to a change in the intensity of the light source, like the double wavelength spectrometry method described above, a prior art method that is one kind of the double wavelength spectrometry will now be explained with reference to FIG. 1.

FIG. 1 is a block diagram of a filter correlation infrared analyzer in which an infrared beam 121 radiated from an infrared source 101 is transmitted through a sample cell 102. An infrared beam 122, which is transmitted from the sample cell 102, is transmitted to a modulator 103. The sample cell 102 is a pipe in which infrared transmission windows are disposed on both ends thereof and which includes an inlet and an outlet on the near places from the both ends. An interesting component in a sample gas flowing through the sample cell absorbs infrared of a specific wavelength, and the infrared beam 122 transmitted through the sample cell 102 loses the energy at the specific wavelength. The modulator 103 is a rotating disk with filters mounted thereon, where one of the filters is a sensing filter 104 whose maximum transmission wavelength is equal to the specific wavelength absorbed by the interesting component, and the other filter is a reference filter 105 whose maximum transmission wavelength is different from the specific wavelength. By rotating the modulator, the filters periodically cross the infrared beam 122 transmitted through the sample cell 102. The infrared beam 122 transmitted through the sample cell 120 is modulated by the beam being transmitted through the sensing filter 104 and the reference filter 105 alternately. The modulated infrared beam 123 is focused on an infrared sensor 108 by a focusing lens 107, and the modulated infrared beam 123 is detected as an electric signal. The detected electric signal is amplified by a head amplifier 110, and is then output to a synchronous rectifier 111. On the other hand, a synchronous signal detector 106 detects a synchronous signal of the modulator 103, and transmits the synchronous signal to a phase adjuster 109. The phase adjuster 109 adjusts the synchronous signal and outputs the signal in the synchronous rectifier 111. The synchronous rectifier 111 rectifies the electric signal synchronizing with the synchronous signal, and thereby obtains a measured signal corresponding to the concentration of the interesting component in the sample.

By more careful consideration, the gaseous or liquid samples contain many coexisting components with the interesting component. Some of the components interfere with analyzing the interesting component, such as water vapor in the case of analyzing nitrogen mono-oxide in flue gas and water or electrolytes in water in the case of analyzing glucose dissolved in water.

Details of the interference caused by the coexisting components will be described with reference to FIG. 2. A spectrum of interfering components 152 has no peak at an absorption wavelength of the interesting component 153 but tails over it. Even if the slope of the tailing is small, the tailing often causes fatal errors in the analysis results because of an increasing concentration of the interfering components. The double wavelength spectrometry often has a problem in that the tailing of spectrum of the interfering components causes fatal errors in the analysis results even if the reference wavelength 154 is selected near the absorption wavelength of the interesting component 153.

Accordingly, an objective of the present invention is to provide an analyzing apparatus which removes the interference caused by the tailing spectrum of the interfering components, and which determines an exact concentration of the interesting component by measuring the light absorption of the interesting component. It is a further object of the present invention to provide a convenient and inexpensive analyzing apparatus capable of measuring interesting components in a manner that is neither destructive nor invasive to a person.

SUMMARY OF THE INVENTION

The present invention provides an interference filter transmission wavelength scanning photometer for determining the concentration of an interesting component in a sample without interference from the coexistent components by measuring the light absorption of the interesting component.

The photometer of the present invention comprises a light source, an interference filter operable to scan a transmission wavelength periodically, an infrared sensor, and a zero cross detector.

The photometer of the present invention can determine the concentration of an interesting component in a sample without interference from coexisting components in the sample by an operation comprising the following steps:

deciding a range for scanning the transmission wavelength of the interference filter so that the center of a small change of a wavelength induced by periodically scanning the transmission wavelength is equal to an absorption wavelength of the interesting component;

detecting an intensity of a light beam from the light source as an electric signal by the infrared sensor in which the light beam is provided to, after the light beam is transmitted through the interference filter and is transmitted to or reflected from the sample placed to the front or rear of the interference filter;

obtaining a full period T (the time for every other zero cross point of the AC component) and a half period $T_1$(the time between the rise and fall of a zero cross point of the AC component) which the zero cross detector detects from the AC component of the electric signal;

determining the concentration of the interesting component by calculating a ratio according to the expression $(T-2T_1)/T$.

Incidentally, a number of methods for scanning the transmission wavelength of the interference filter are well-known. One method scans the transmission wavelength by changing the refractive index of a spacer layer of gas which pressurizes up and down, which operates to keep the displacement between metal layers constant. In another method, a displacement between metal layers is changed so as to scan the transmission wavelength. In yet another method, which is suitable for the present invention, the transmittance wavelength is scanned by inclining the normal of the interference filter to the optical axis. The best mode for carrying out the present invention is an interference filter transmission wavelength scanning photometer wherein the transmission wavelength is scanned by swinging the interference filter periodically, which is achieved by inclining the normal of the interference filter to the optical axis.

Figure 1:
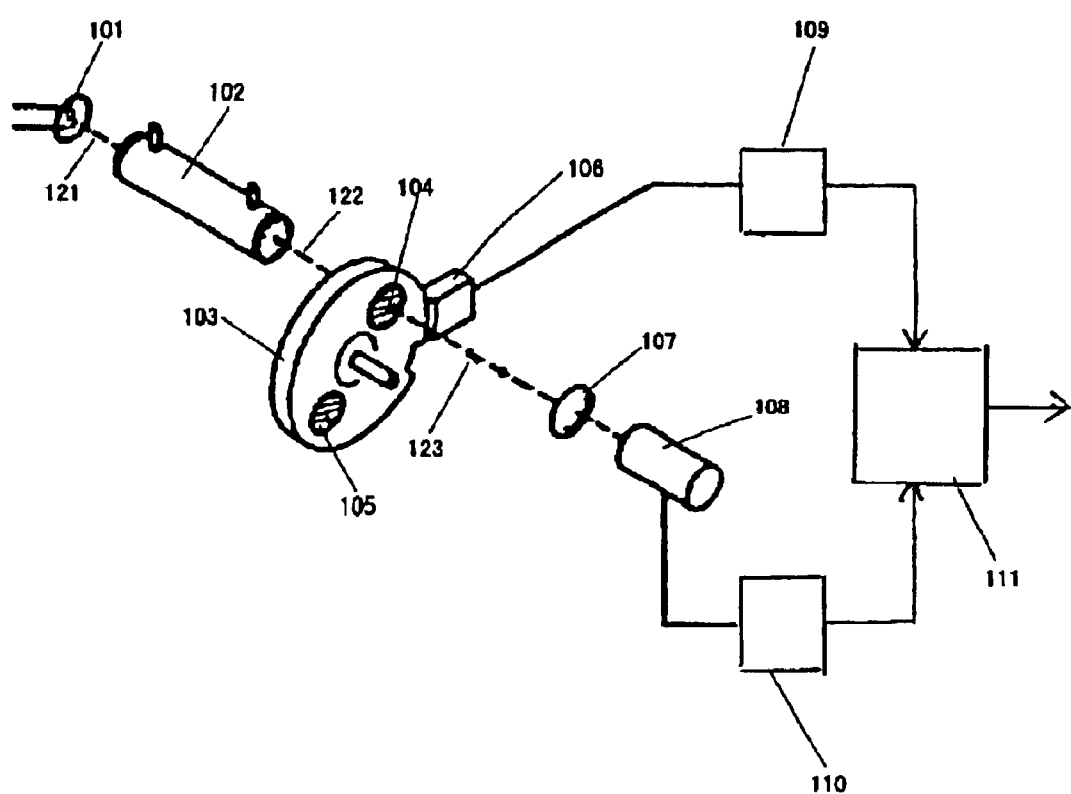
FIG. 1 is a block diagram of a filter correlation infrared analyzer as an example of the prior art.

Reference numerals in the drawings denote the following elements.

1 a light source
2 a long wavelength pass filter
3 an interference filter
4 an axis
5 S-poles
6 N-poles
7 forcing coils
8 a lens
9 a quartz rod
10 a sample
11 an infrared sensor
12 an oscillation circuit
13 a head amplifier
14 an alternating amplifier
15 a zero cross detector
16 a microprocessor
17 a display device
18 a keyboard
19 a communication port
31 a quartz rod
32 a header
33 an infrared sensor
34 a human lip
35 a suction pump
36 a suction pressure regulator
101 an infrared source
102 a sample cell
103 a modulator
104 a sensing filter
105 a reference filter
106 a synchronous signal detector
107 a focusing lens
108 an infrared sensor
109 a phase adjuster
110 a head amplifier
111 a synchronous rectifier
121 an infrared beam
122 an infrared beam transmitted through the sample cell 102
123 a modulated infrared beam
151 a spectrum of an interesting component
152 a spectrum of interfering components
153 an absorption wavelength of an interesting component
154 a reference wavelength
161 a short wavelength limit
162 a long wavelength limit 163 a high transmittance limit
164 a low transmittance limit
165 a transmittance for containing no interesting component
166 a transmittance for containing an interesting component
171 a spectrum of an interference filter inclined at an angle of 15 degrees between its normal and the optical axis
172 a spectrum of an interference filter inclined at an angle of 20 degrees between its normal and the optical axis
173 a spectrum of an interference filter inclined at an angle of 25 degrees between its normal and the optical axis
181 an electric signal due to interfering components
182 an electric signal due to an interesting component
183 an actually observed signal

DETAILED DESCRIPTION OF THE INVENTION

The preferred embodiment of an interference filter transmission wavelength scanning photometer of the present invention and the principle for determining a concentration of an interesting component will now be described in detail with reference to the attached drawings.

In the present invention, an interference filter is swung periodically to incline a normal of the interference filter to an optical axis. The peak transmission wavelength of the interference filter is thereby scanned, as shown in FIG. 2, in a narrow range between a short wavelength limit 161 and a long wavelength limit 162 around an absorption wavelength of an interesting component 153 in a sample.

Figure 3:
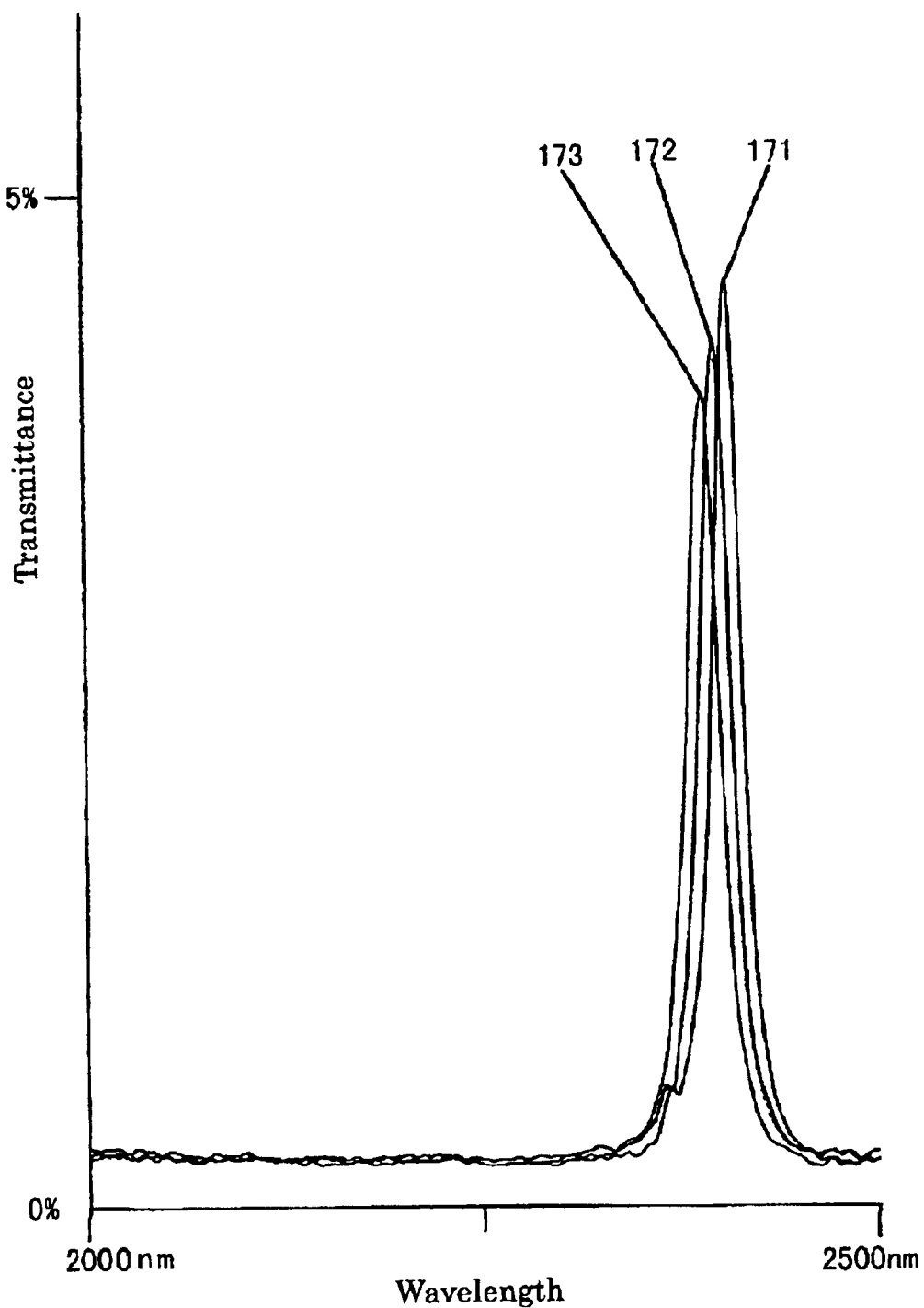
FIG. 3 is a spectrogram showing spectra of an interference filter when the normal of the interference filter is inclined to the optical axis.

It is well-known that the transmission wavelength of the interference filter is changed by inclining the normal of the interference filter to the optical axis. FIG. 3 shows experimental spectra 171, 172 and 173 of an interference filter which is inclined at an angle of 15, 20 and 25 degrees between its normal and the optical axis, respectively. The maximum transmission wavelengths are 2289 nm, 2273 nm and 2257 nm, respectively. (The scale of the horizontal axis of all spectrogram are linear to wave numbers, but all numerical expressions are converted into wavelengths for a consistent description.)

Figure 2:
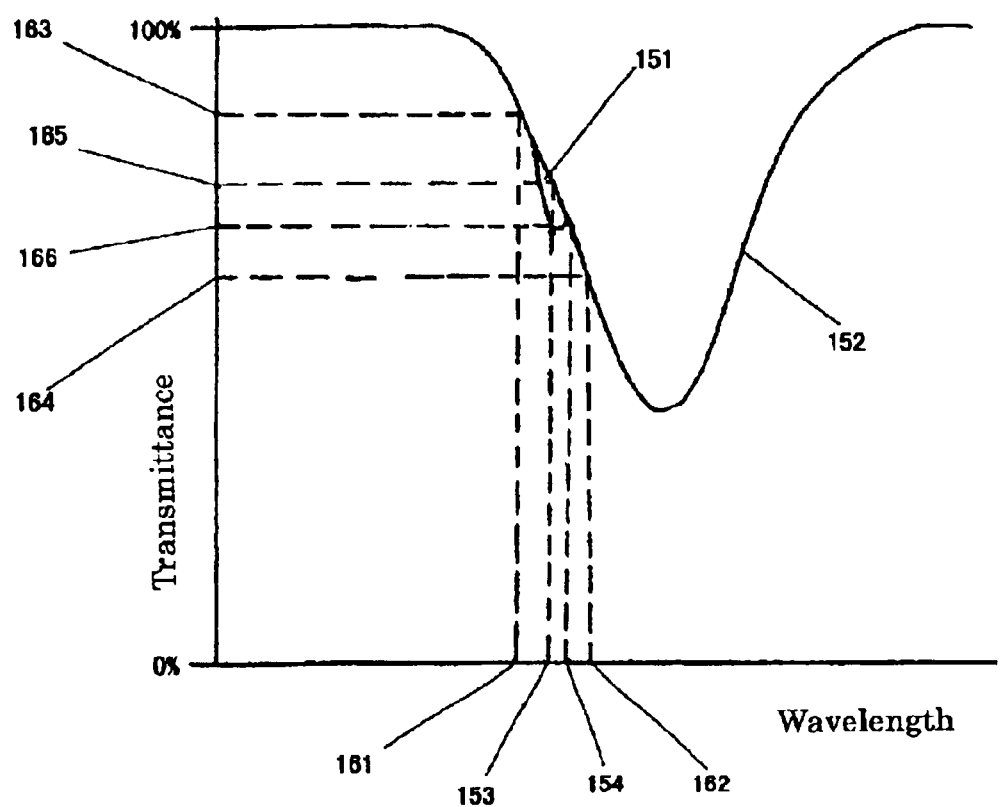
FIG. 2 is a spectrogram showing a relation between a spectrum of an interesting component and a spectrum of interfering components.
Figure 4:
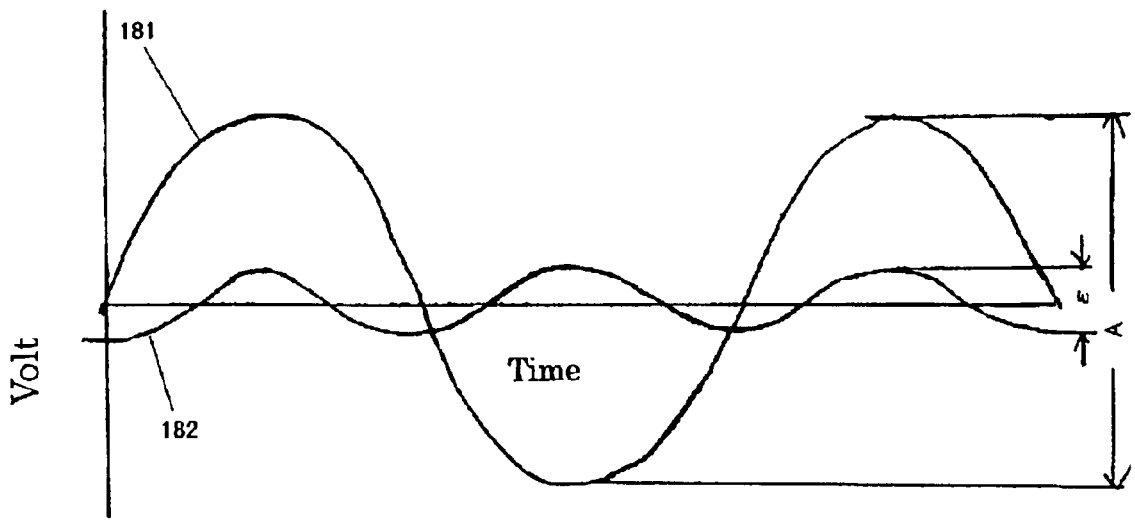
FIG. 4 is a chart showing a relation between an electrical signal due to an interesting component and an electrical signal due to interfering components.
Figure 4:
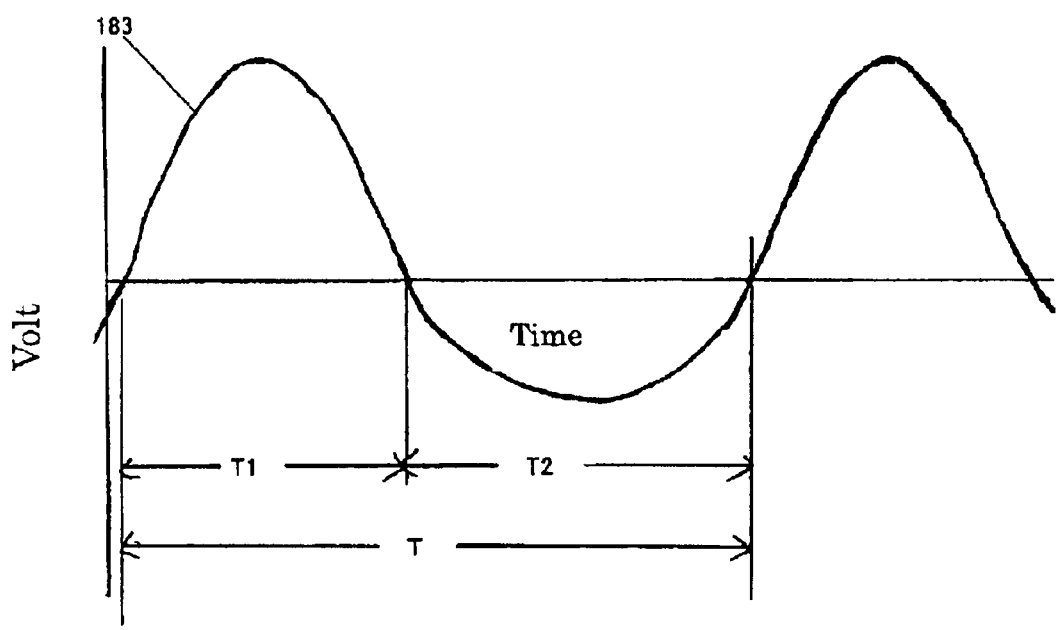

Transmittance, which is observed after light beam transmits through the sample having a spectrum of interfering components as shown in FIG. 2, varies periodically from a high transmittance limit 163 to a low transmittance limit 164 by changing the maximum transmission wavelength from the short wavelength limit 161 at the angle of 25 degrees between the normal of the interference filter and the optical axis to the long wavelength limit 162 at the angle of 15 degrees between the normal of the interference filter and the optical axis. An electric signal which is proportional to the intensity of the light beam transmitting through the sample is detected by an infrared sensor, and the detected electric signal is varied periodically like an electric signal due to the interfering component 181, as shown in FIG. 4. It is defined here that the electric signal due to the interfering component 181 takes a maximum positive value when the angle between the normal of the interference filter and the optical axis is 25 degrees, that is, at the high transmittance limit 163, and a minimum negative value between the normal of the interference filter and the optical axis when the angle is 15 degrees, that is, at the low transmittance limit 164.

Continuously, it will now be explained what happens when an interesting component in the sample is increased. By increasing the interesting component, a spectrum of the interesting component 151, as shown in FIG. 2, is enlarged. When the spectrum 151 is enlarged, transmittance to the wavelength at the center angle between 15 and 25 degrees decreases from a transmittance for containing no interesting component 165 to a transmittance for containing the interesting component 166. By decreasing the transmittance, the electric signal due to the interesting component 182, as shown in FIG. 4, joins in the electric signal due to the interfering components 181, and the electric signal due to the interesting component 182 has negative peaks which occur when the electric signal due to the interfering components 181 is in the middle between its maximum and minimum values. After increasing the interesting component, an actually observed signal 183 is a synthetic electrical signal which is the sum of the electric signal due to the interfering components 181 and the electric signal due to the interesting component 182. The information which has to be obtained corresponds to the amplitude of the electric signal due to the interesting component 182.

Further explanation about how to obtain the information corresponding to the amplitude of the electrical signal due to the interesting component 182 from the actually observed signal 183 will now be given. The electric signal due to the interfering components 181 is large and is expressed according to the following equation, $$F = A\sin\omega t,$$

where F is the electric signal due to the interfering components 181, A is its amplitude, and $\omega$ is the angular frequency which is expressed according to $\omega = 2\pi/T$ when T is a full period. As the electric signal due to the interesting component 182 is extremely smaller than the electric signal F, it is difficult to observe any change in the electric signal F because it is joined with the electric signal due to the interesting component 182. But, by paying attention to zero cross points, which are points that occur when the electric signal F is zero, an increase of the amplitude of the electric signal due to the interesting component 182 lets the electric signal F at the zero cross points down as a variation of $(\frac{1}{2})\epsilon$, where $\epsilon$ is an amplitude of the electric signal due to the interesting component 182.

Here, time lags at the zero cross points are estimated when the electric signal F at the zero cross points is let down as the variation of $(\frac{1}{2})\epsilon$. The electric signal F is differentiated according to the following equation for obtaining slopes of the electric signal F at the zero cross points.

$$dF/dt = A\omega \cos \omega t$$

Slopes at the phase of $\omega t = \pi$ and $\omega t = 2\pi$ are $-2\pi A/T$ and $2\pi A/T$, respectively. By letting the electric signal F at the zero cross points down as the variation of $(\frac{1}{2})\epsilon$, the time lags at the zero cross points of the electric signal F are $\epsilon T/(4\pi A)$ fast at the phase of $\omega t = \pi$ and $\epsilon T/(4\pi A)$ slow at the phase of $\omega t = 2\pi$. A time difference between a prolonged half period $T_2$ and a shortened half period $T_1$, of the actually observed signal 183 is obtained according to the following expression by the above-described estimation.

$$T_2 - T_1 = \epsilon T/(\pi A)$$

The ratio of the time difference to the full period T is calculated by $(T_2-T_1)/T = \omega/(\pi A)$, and this result indicates that the ratio is proportional to the amplitude $\epsilon$ of the electrical signal due to the interesting component 182. This study demonstrates that it is possible to determine the concentration of the interesting component without interference from the coexisting components by examining in the full period (T) and the one half period ($T_1$), while the other half period $T_2$ is used to calculate the difference between the full period T and the one half period $T_1$.

Figure 5:
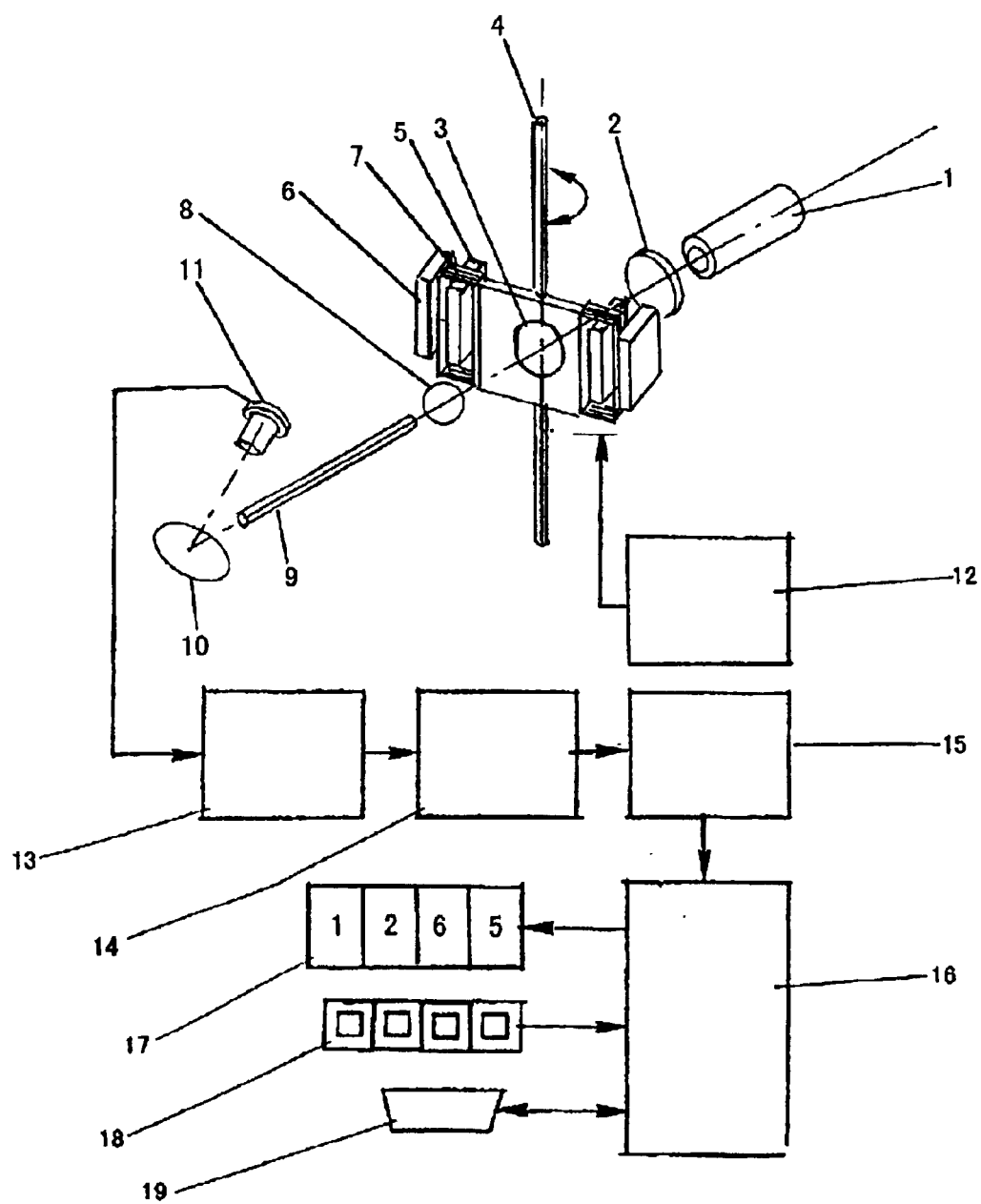
FIG. 5 is a block diagram showing an interference filter transmission wavelength scanning photometer according to the preferred embodiment of the present invention.

Construction of the interference filter transmission wavelength scanning photometer of the present invention will now be explained with reference to FIG. 5. FIG. 5 is separated into two parts. That is, one part of FIG. 5 is a diagram of an optical layout of the interference filter transmission wavelength scanning photometer of the present invention, and another part is a block diagram of the electric circuits of the interference filter transmission wavelength photometer of the present invention. In FIG. 5, shorter wavelengths of the light beam originating from a light source 1 are filtered out by a long wavelength pass filter 2, while longer wavelengths of the light beam pass through the long wavelength pass filter 2 and proceed ahead to an interference filter 3. The interference filter 3 is fixed with forcing coils 7 on both sides of the interference filter 3 and can swing centering an axis 4. S-poles 5 and N-poles 6 of a magnet are installed on both sides of the wirings of the forcing coils 7 and provide an alternating current to the forcing coils 7. By providing the forcing coils 7 with alternating current, the interference filter starts to swing centering around the axis 4. The angle between the normal of the interference filter 3 and the optical axis is initially set at an angle of 20 degrees so that the angle changed by the swinging of the interference filter 3 is within an angle between 15 to 25 degrees.

A light beam modulated by swinging the interference filter 3 is focused on an end surface of a quartz rod 9 by a lens 8. The quartz rod 9 guides the light beam near to a sample 10, and the light beam from the other end surface of the quartz rod irradiates the sample 10. Part of the light beam reflected on the surface of the sample is provided to an infrared sensor 11. The light beam which is modulated by swinging the interference filter and reflected on the sample 10 is detected by the infrared sensor 11 as an electric signal. The electric signal is then sent to the electric circuits part as illustrated in FIG. 5.

In the electric circuits part of the interference filter transmission wavelength photometer of the present invention, an oscillation circuit 12 supplies the alternating current to the forcing coils 7 so as to swing the interference filter 3. It is extremely important to keep the swinging of the interference filter stable, because the swinging of the interference filter, which is forced by the alternative current, is the origin of all of the signals. Therefore, a feedback control system is adopted to keep the energy swinging the interference filter constant. The swinging velocity is measured by sensing coils, which are placed at the same position as the forcing coils 7. The electric signal which is induced in the optical system and detected by the infrared sensor 11 is amplified by a head amplifier 13, and the AC component of the detected electric signal is amplified by an alternating amplifier 14 and output to a zero cross detector 15. The detected electrical signal has a frequency that is basically decided by the swinging frequency of the interference filter. The zero cross detector 15 generates an interrupt signal which informs a microprocessor 16 of the times when the rising or falling electric signals cross the zero level. The microprocessor 16 memorizes the times of each of the zero cross points through the aid of an inner timer. The full period T is obtained as the time from the rising zero cross point to the next rising zero cross point, and the half period $T_1$, is obtained as the time from the rising zero cross point to the next falling zero cross point. After acquiring data for a certain integrating time, a remainder obtained by subtracting twice the value of an integrated half period $\Sigma T_1$ from an integrated full period $\Sigma T$ that is divided by the integrated full period $\Sigma T$ gives a ratio that is defined as a distortion factor herein. After the concentration of the interesting component (for instance, glucose concentration in blood for a glucose meter) has been calibrated by using the distortion factors, the concentration of the interesting component is determined by the distortion factor, and the concentration value of the interesting component is displayed and communicated. A display device 17, which displays a concentration value, etc., a keyboard by which the analytical apparatus of the present invention is operated, and a communication port 19 through which a plurality of information including the measuring value can be communicated are mounted with/on the microprocessor 16.

Working Example of the Present Invention

A working example of the present invention for determining the concentration of glucose in blood is now described.

Figure 6:
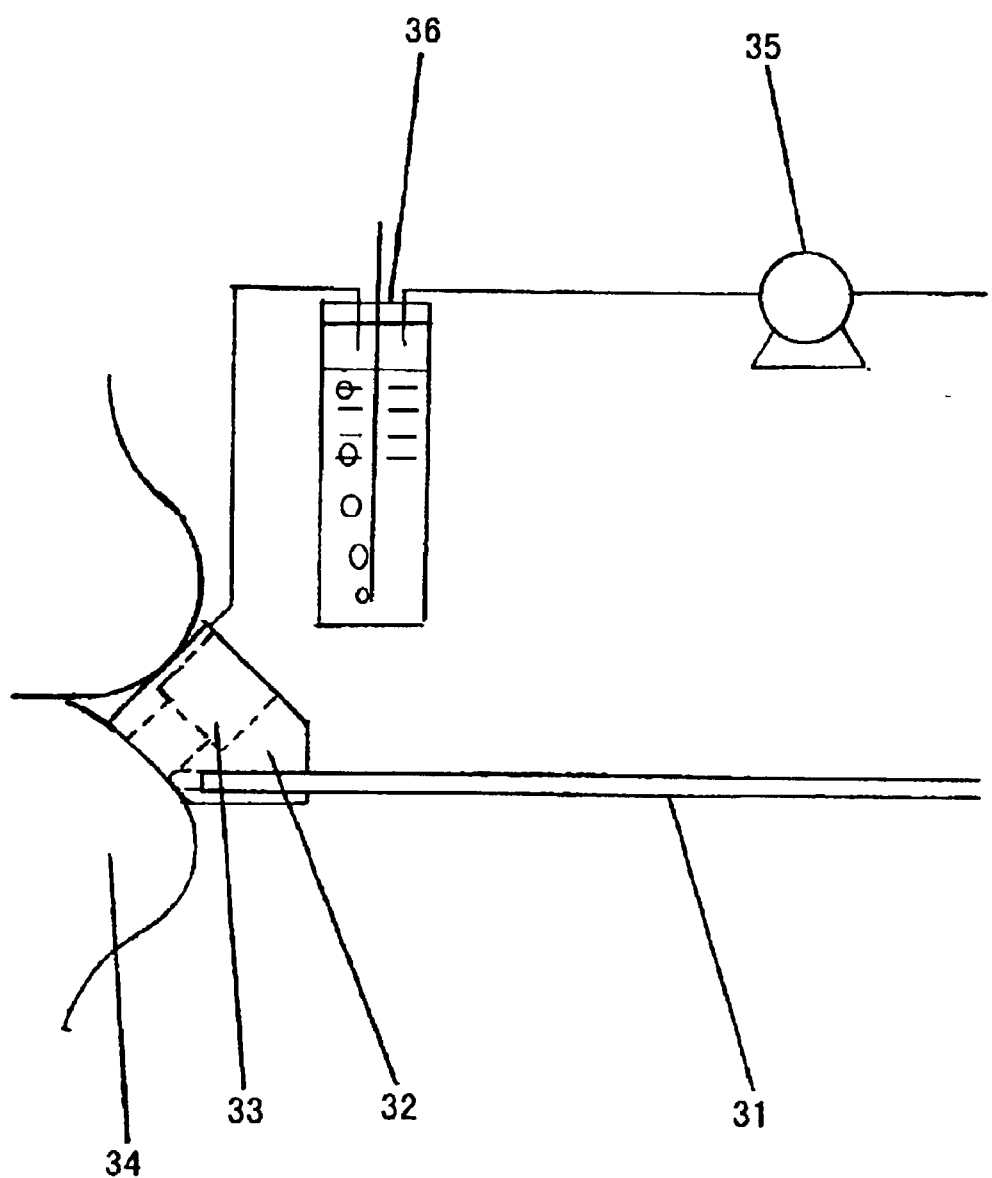
FIG. 6 is a sketch illustrating an optical sampling system by which an optical signal corresponding to the concentration of glucose in blood is obtained from a human lip.

The human lip has a mass of capillary blood vessels under its outermost skin, and the red lip is visible to the naked eye. The interference filter transmission wavelength scanning photometer of the present invention is applied for determining the concentration of glucose in the blood by diffuse reflectance on the outermost skin of the lip. An optical sampling system is shown in FIG. 6. Quartz rod 31 is equivalent in function and effect to the quartz rod 9 described with reference to FIG. 5. Header 32 holds the quartz rod 31, which guides the light beam to the human lip 34, and an infrared sensor 33, which detects the reflecting light on the human lip 34. A suction pump 35 with a suction pressure regulator 36 sucks a cavity between the human lip 34 and the infrared sensor 33 so as to affix the surface of the human lip 34 to the header 32.

Figure 7:
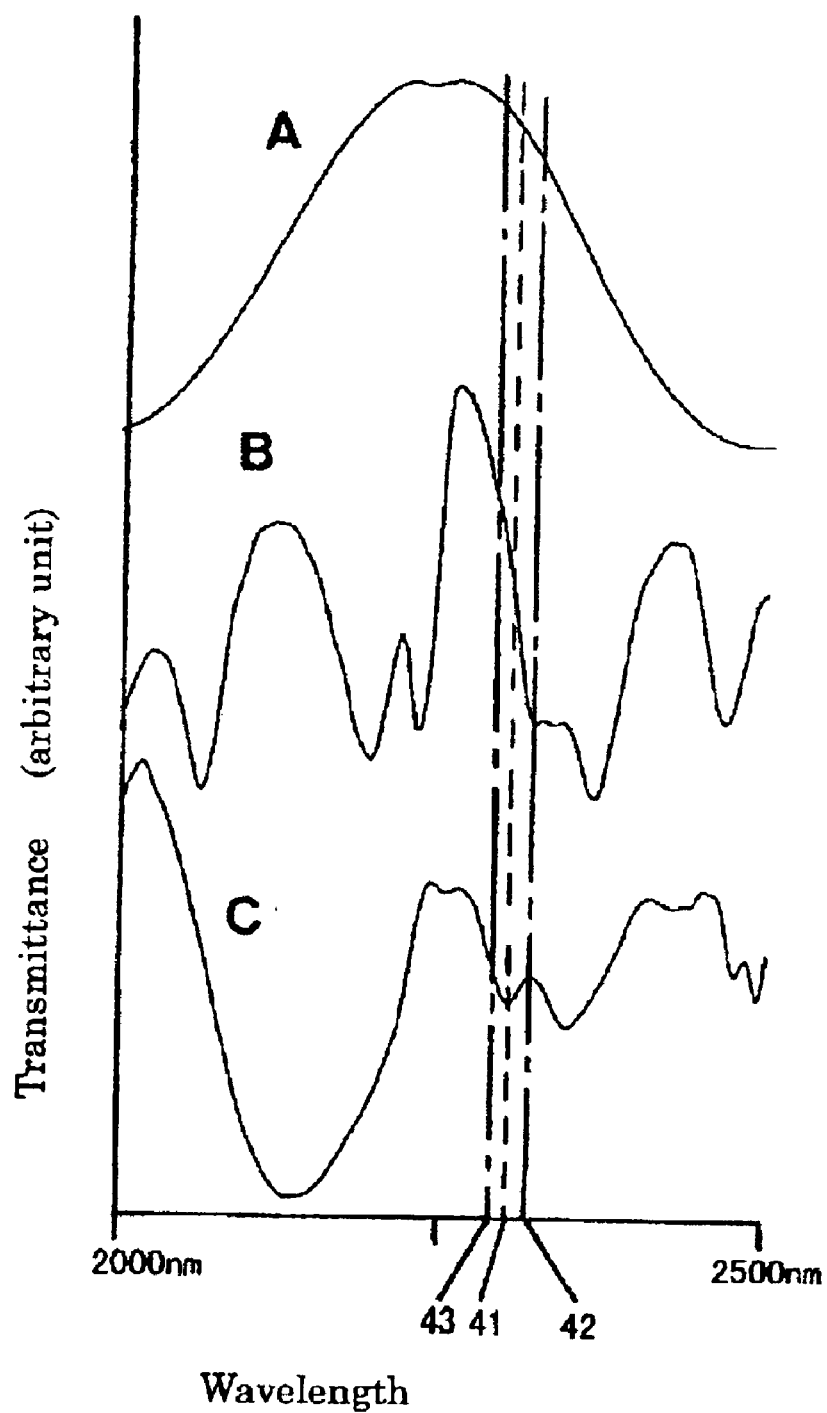
FIG. 7 is a spectrogram of the main components that a sample is composed of for illustrating a working example of the present invention.

FIG. 7 illustrates spectra of the main components in the blood. A spectrum of water in the blood is denoted by letter A, a spectrum of blood paste removed the water in the blood is denoted by letter B, and a difference spectrum of the glucose in the water obtained by subtracting the spectrum of the water is denoted by letter C in FIG. 7.

It has been designed, in the working example of the present invention, that a change in the transmittance of the glucose at the wavelength of 2273 nm (the position denoted by reference numeral 41) has been adopted for determining the concentration of the glucose in the blood. The transmission wavelength of the interference filler changes from a maximum of 2289 nm (the position denoted by reference numeral 42) to a minimum of 2258 nm (the position denoted by reference numeral 43), and thus centers at 2273 nm (position 41). Other specifications for the instrumental design of the present invention are shown below.

Specifications for the Instrumental Design of the Present Invention frequency of swinging the interference filter: 150 Hz
quartz rod: outer diameter of 1.5 mm, and length of 160 mm
timer clock for measuring period: 8 MHz
data integrating time: 300 second
clock of microprocessor: 8 MHz According to the above-described specifications for the instrumental design of the present invention, a prototype of the interference filter transmission wavelength scanning photometer has been experimentally manufactured. By using this prototype, the glucose concentration in blood has been determined in a non-invasive manner. Data for each data integrating time are divided into ten sections, and distortion factors for the sections are calculated. A measuring value for each data integrating time is an average of six medians from ten calculated distortion factors.

Figure 8:
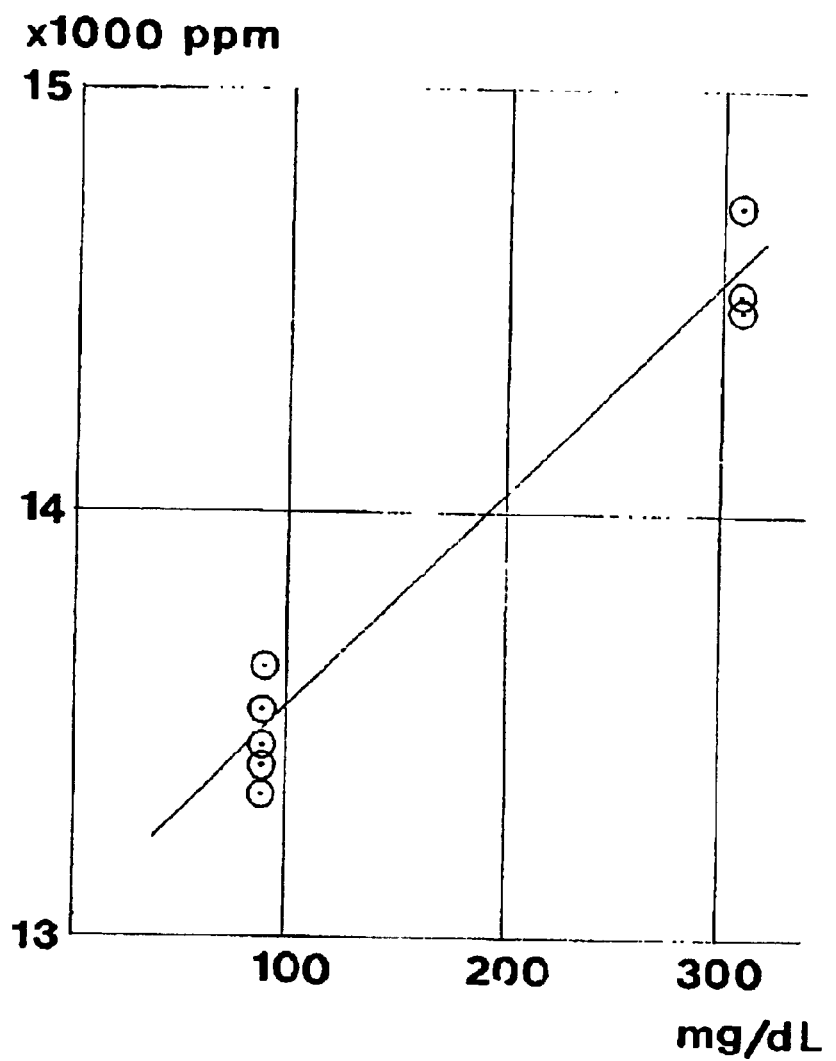
FIG. 8 is a correlation plot comparing values of the concentration of glucose in human blood measured by an interference filter transmission wavelength scanning photometer of the present invention to values of the concentration of glucose in human blood measured by a commercial glucose meter.

The glucose concentration in the blood of a healthy test person with an empty stomach has been measured to be 89 mg/dL by a commercial glucose meter. Keeping this condition, the interference filter transmission wavelength scanning photometer of the present invention has been applied for determining the glucose concentration in the blood, and five measuring values have been obtained. Consequently, between 40 minutes and 70 minutes after a time when the test person drank a cup of syrup, which was hot water dissolved with glucose of 75 g, three measuring values have been obtained. At 60 minutes after the time when the test person drank a cup of the syrup, the glucose concentration in the blood of the test person was measured to be 308 mg/dL by the commercial glucose meter. Assuming that the glucose concentration in the blood of the test person has been regarded as constant between 40 minutes and 70 minutes after the time when the test person drank a cup of the syrup, a correlation plot obtained by these experiments is shown in FIG. 8. It is preferably a desirable result that a coefficient of correlation between the measured value obtained by the interference filter transmission wavelength scanning photometer of the present invention and the glucose concentration in the blood obtained by the commercial glucose meter is 0.98.

It has thus been shown that a non-invasive determination of the glucose concentration in blood is possible with the interference filter transmission wavelength scanning photometer according to the present invention.

Determination of the concentration of the interesting component by measuring the light absorption of the material has desirable features such as being non-destructive and non-invasive to a person. But in many cases, as the tailing of the spectra of coexisting components overlaps the absorption wavelength of the interesting component, it is difficult to determine the concentration of the interesting component by using only one wavelength. Therefore, numerous wavelengths are used for the determination of the concentration of the interesting component, after all a spectrometry is applied for it. Although such a spectrometry has numerous application fields, it needs large equipment and is expensive. With these reasons, the analyzing apparatus for measuring the light absorption of the material is desirable, but is not used so commonly. For example, there is no glucose meter for measuring the light absorption of the material in the Japanese market, although many glucose meters implementing an enzymatic method are commonly used.

The present invention, even with a simple composition, is able to achieve the same performance as the spectrometry for one component in the sample. The present invention is industrially valuable, because the present invention provides a desirable feature for determining the concentration of the interesting component, by measuring the light absorption of the material. Thus, the present invention has developed an analytical apparatus having accurate results and a lower cost, and it contributes technically to industrial fields, environmental pollution control, and medical fields.

What is claimed is:

1. An interference filter transmission wavelength scanning photometer for determining a concentration of an interesting component in a sample without interference from coexistent components by measuring the light absorption of the interesting component, said photometer comprising:

a light source;

an interference filter operable to scan a transmission wavelength periodically;

an infrared sensor; and a zero cross detector;

said photometer having functions to determine the concentration of the interesting component in the sample by operations comprising:

deciding a range of scanning the transmission wavelength of said interference filter so that a center of a small change in a wavelength induced by scanning the transmission wavelength periodically is equal to an absorption wavelength of the interesting component;

detecting an intensity of a light beam output from said light source as an electric signal by said infrared sensor in which the light beam is provided to after the light beam is transmitted through said interference filter and after the light beam is transmitted or reflected on the sample placed to the front or rear of said interference filter;

obtaining a full period T, which is a period of time between every other zero cross point of an AC component of the electric signal, and a half period $T_1$, which is a period of time between each zero cross point of the AC component of the electric signal which said zero cross detector is operable to detect from the electric signal; and determining the concentration of the interesting component by calculating a ratio expressed by $(T-2T_1)/T$.

2. The interference filter transmission wavelength scanning photometer according to claim 1, wherein the transmission wavelength is scanned by swinging said interference filter periodically so as to incline the normal of said interference filter to an optical axis.

3. An interference filter transmission wavelength scanning photometer operable to determine a concentration of an interesting component in a sample without interference from coexisting components by measuring the light absorption of the interesting component, said photometer comprising:

a light source operable to output a light beam;

an interference filter operable to scan a transmission wavelength periodically within a range so that a center of a small change in a wavelength induced by scanning the transmission wavelength periodically is equal to an absorption wavelength of the interesting component, and to pass the light beam outputted from said light source therethrough to be transmitted on the sample located to the front or rear of said interference filter;

an infrared sensor operable to receive the light beam outputted from said light source after the light beam is transmitted through said interference filter and transmitted or reflected on the sample, and to detect an intensity of the light beam upon receiving the light beam;

a zero cross detector operable to detect a full period T corresponding to a period of time between every other zero cross point of an AC component of the electric signal and a half period $T_1$, corresponding to a period of time between each zero cross point of the AC component of the electric signal; and a determining unit operable to determine the concentration of the interesting component by calculating a ratio expressed by $(T-2T_1)/T$.

4. The interference filter transmission wavelength scanning photometer according to claim 3, wherein the transmission wavelength is scanned by swinging an interference filter periodically so as to incline a normal of said interference filter to an optical axis.

5. The interference filter transmission wavelength scanning photometer according to claim 4, wherein said interference filter is swung periodically so that an angle between the normal of said interference filter and the optical axis is between 15 and 25 degrees.

6. The interference filter transmission wavelength scanning photometer according to claim 3, further comprising a long wavelength pass filter disposed between said light source and said interference filter.

7. The interference filter transmission wavelength scanning photometer according to claim 3, further comprising forcing coils disposed on opposite sides of said interference filter, respectively.

8. The interference filter transmission wavelength scanning photometer according to claim 7, further comprising an S-pole and an N-pole of a magnet disposed on opposite sides of each of said forcing coils for swinging said interference filter responsive to an AC current.

9. The interference filter transmission wavelength scanning photometer according to claim 8, further comprising an oscillation circuit operable to supply the AC current to said S-pole and said N-pole.

10. The interference filter transmission wavelength scanning photometer according to claim 3, further comprising a lens operable to focus the light beam transmitted through said interference filter onto the sample.

11. The interference filter transmission wavelength scanning photometer according to claim 10, further comprising a quartz rod operable to receive the light beam focused by said lens at one end of said quartz rod to direct the light beam onto the sample.

12. The interference filter transmission wavelength scanning photometer according to claim 3, wherein said zero cross detector is operable to output an interrupt signal to said determining unit each time said zero cross detector detects a zero cross point of the AC component of the electric signal.

13. The interference filter transmission wavelength scanning photometer according to claim 3, further comprising a display device operable to display the concentration of the interesting component.

14. The interference filter transmission wavelength scanning photometer according to claim 3, wherein said determining unit is a microprocessor.

* * * * *